(12) United States Patent
Duger (10) Patent No.: US 9,610,177 B2
(45) Date of Patent: Apr. 4, 2017

(54) VACUUM UNIT

(71) Applicant: Ortotek Ortopedi Protez Ortez Rehabilitasyon Merkezi Tic.Ltd.Sti, Ankara (TR)

(72) Inventor: Mustafa Duger, Ankara (TR)

(73) Assignee: ORTOTEK ORTOPEDI PROTEZ ORTEZ REHABILITASYON MERKEZI TIC. LTD. STI, Ankara (TR)

( * ) Notice: Subject to any disclaimer, the term of this patent is extended or adjusted under 35 U.S.C. 154(b) by 249 days.

(21) Appl. No.: 14/363,808

(22) PCT Filed: Sep. 17, 2013

(86) PCT No.: PCT/TR2013/000295
§ 371 (c)(1),
(2) Date: Jun. 8, 2014

(87) PCT Pub. No.: WO2014/109720
PCT Pub. Date: Jul. 17, 2014

(65) Prior Publication Data
US 2016/0235559 A1    Aug. 18, 2016

(30) Foreign Application Priority Data
Jan. 10, 2013 (TR) .................................. 2013/00341
Aug. 2, 2013 (TR) .................................. 2013/09443

(51) Int. Cl.
*A61F 2/66* (2006.01)
*A61F 2/80* (2006.01)
*A61F 2/74* (2006.01)

(52) U.S. Cl.
CPC .............. *A61F 2/6607* (2013.01); *A61F 2/80* (2013.01); *A61F 2002/742* (2013.01); *A61F 2002/802* (2013.01); *A61F 2002/805* (2013.01)

(58) Field of Classification Search
CPC .. A61F 2/80; A61F 2/66; A61F 2/6607; A61F 2002/802; A61F 2002/742
See application file for complete search history.

(56) References Cited

U.S. PATENT DOCUMENTS

| | | | |
|---|---|---|---|
| 6,855,170 B2 * | 2/2005 | Gramnas | A61F 2/66 623/49 |
| 2009/0036998 A1 * | 2/2009 | Finlinson | A61F 2/78 623/34 |

(Continued)

FOREIGN PATENT DOCUMENTS

| DE | 1002504 B | 2/1957 |
|---|---|---|
| DE | 202006019257 U1 | 3/2007 |

(Continued)

*Primary Examiner* — Bruce E Snow
(74) *Attorney, Agent, or Firm* — Gokalp Bayramoglu (57) ABSTRACT

The present invention is related to a vacuum unit that can suck in the air inside the carrier shell and which can be used as ankles of prosthetic legs. The present invention aims to develop a vacuum unit which enables the suction of air trapped between the stump and the socket of the prosthesis used by the users or patients who are using lower knee or upper knee prosthesis. Another aim of the invention is to provide vacuum without the need to use electrical energy by mechanically driving the piston which enables vacuum. Another aim of the invention besides these is to ensure that there is no need for a different/special motion by means of the triggering the piston motion within the vacuum medium via the force obtained from natural walking motions.

2 Claims, 7 Drawing Sheets

(56) References Cited

U.S. PATENT DOCUMENTS

2012/0143351 A1   6/2012  Tompkins
2014/0371874 A1*  12/2014 Wu .......................... A61F 2/80
                                                    623/47

FOREIGN PATENT DOCUMENTS

EP          0482809 A1   4/1992
WO       WO02/067825 A2  9/2002

* cited by examiner

VACUUM UNIT

TECHNICAL FIELD

The present invention is related to a vacuum unit that can suck in the air inside the carrier shell and which can be used as ankles of prosthetic legs.

BACKGROUND ART

Patients whose limbs have been amputated due to various reasons are using different sorts of prosthesis either to adapt to social life or to increase their standards of living. Said prosthesis is being manufactured with care both in terms of aesthetics and in terms of functionality in order to replace real limbs cosmetically and functionally. Even though simulation of said prosthesis in terms of cosmetics might be possible, it is still not possible for said prosthesis to replace the real limb of a person in terms of functionality.

However the prosthesis parts obtained via studies carried out parallel with technological advancements, it is possible to reach more functional prosthesis parts and prosthesis, which are easier to use. One of such advancements has been described in the patent application file numbered US2012143351; wherein it is aimed to prevent the dislocation of the prosthesis. In the related application a vacuum unit which sucks in the air inside the socket (shell) into which the stub is inserted and which is used in either upper knee or lower knee prosthesis is being described. By means of said vacuum unit, the dislocation of the prosthesis due to the trapped air between the stump and the socket is eliminated. By overcoming such a problem the patients can act as one with their prosthesis in daily usage and it is aimed for them to be less concerned about the dislocation of their prosthesis.

BRIEF DESCRIPTION OF THE INVENTION

The present invention aims to develop a vacuum unit which enables the suction of air trapped between the stump and the socket of the prosthesis used by the users or patients who are using lower knee or upper knee prosthesis. Another aim of the invention is to provide vacum without the need to use electrical energy by mechanically driving the piston which enables vacuum. Another aim of the invention besides these, is to ensure that there is no need for a different/special motion by means of the triggering the piston motion within the vacuum medium via the force obtained from natural walking motions.

BRIEF DESCRIPTION OF THE SEVERAL VIEWS OF THE DRAWING(S)

The vacuum unit in order to reach the aims of the invention has been shown in the attached figures wherein said figures illustrate the following.

The parts in the figures have each been numbered and the references of said numbering have been listed below.

1. Vacuum unit
2. Upper body
3. Lower body
4. Ankle shaft
5. Piston head
6. Motion transfer group
7. Upper body connection
8. Lower body connection
9. Lower body chain link
10. Forked chain link
11. Piston chain link
12. Front socket
13. Rear socket
14. Front screw
15. Rear screw
16. Tightening means (rubber)

DETAILED DESCRIPTION OF THE INVENTION

The vacuum unit (1) subject to the invention comprises an upper body (2) and a lower body (3) wherein both these body (2 and 3) components are formed by coupling them by the usage of an ankle shaft (4) such that it shall carry out an angular motion. Said angular motion moves the piston head (5) which is located inside the upper body (2) thus enabling the vacuum to be carried out by the vacuum unit (1).

The angular motion carried out by the lower body (3) needs to be converted into a linear motion in order for the piston head (5) providing vacuum moves at a linear direction. This conversion is realized by converting the angular motions carried out by the lower body (3) in relation to the upper body (2) into linear motions by means of the motion transfer group (6).

The angular motion is established around the ankle shaft (4) of the lower body (3) in relation to the upper body (2). The ankle shaft (4) is a shaft which connects both bodies (2 and 3). The upper surface of the lower body (3) is a plane.

None the less the front and rear sections of the lower face of the upper body (2) facing the lower body (3) have front angular volumes (OAH) and rear angular volumes (AAH) that are angled to enable angular movements. By this means the motions carried out by the upper body (2) while the lower body (3) is fixed can be carried out without any prevention from the lower body (3).

The linear motion that needs to be carried out during the closure on to the front angular volume (OAH) and rear angular volume (AAH) is produced by means of the motion transfer group (6) located inside the upper body (2). The lower body connection (8) is used primarily in order to determine the lower body (3) movements. Said lower body connection (8) is an extension of the lower body (3) wherein said extension moves together with the lower body (3).

The position during the motion carried out by the lower body connection (8) around the ankle shaft (4) gets closer to and further from the upper body connection (7). A series of chain links are used in order to pull the piston head (5) upwards when the position gets closer and to pull the piston head back when the position becomes distant. Said chain links are respectively a lower body chain link (9), forked chain link (10) and piston chain link (11) connected to the lower body connection (8).

When the lower body connection (8) gets closer to the upper body connection (7) the lower body chain link (9) pushes the forked chain link (10). During said pushing motion, as one end of the forked chain link (10) is connected to the upper body (2) the forked chain link (10) moves upwards. The piston chain link (11) pushes the piston head (5) such that it moves upwards in order for this motion to be converted into a linear motion that pushes the piston head (5).

The piston head (5) is enabled to be pushed upwards by means of the closing motion of the lower body (3) towards the rear angular volume (AAH) via the movements of the chain links explained above. And on the contrary the piston head (5) is enabled to be pushed downwards by means of the closing motion of lower body towards the front angular volume (OAH) via the movements of the chain links.

The pumping and suction of air can be carried out by using the pumping and suction motion created by said up and down movements. Single sided valves are placed at the air suction and pumping directions inside the volume (H) which is above said piston head (5), depending on the place of application of the invention and the requirements, in order to arrange said effects.

The primary aim of the vacuum unit (1) subject to the invention, is to be able to increase the operation height of the piston head (5) during said air suction and pumping motions without increasing the dimensions of the upper body (2) at the same time. In order to increase the ranges of said study, the angular motion range of the lower body (3) is increased either by increasing the front angular volume (OAH) or by increasing the rear angular volume (AAH).

Usually, despite the rear angular movement provided by correctly stepping on the heel rubber of the prosthesis, the front angular movement cannot be provided as front angular volume (OAH) is not present. By means of the front angular volume (OAH) that the vacuum unit (1) subject to the invention comprises, it is enabled for the upper components of the vacuum unit to be able to lean forward with acute angles instead of a 90 0 angle all the time at the front, in relation to the foot.

According to the preferred application of the invention, in order to complete the step taken by the patient using a vacuum unit (1), initially the leg with the vacuum unit (1) needs to be thrust forward and the patient has to step on the heel. By stepping on the heel, a load is exerted on the rear angular volume (AAH) and said volume is closed due to said load. At this moment when the piston head (5) moves upward the air is pumped out. Following this, the patient is at a vertical position and when the patient transfers all her/his weight to the centre of the vacuum unit's (1) foot the rear angular volume (AAH) and the front angular volume (OAH) reach standard dimensions. At this time as the force exerted on the heel is decreased the piston head (5) moves downwards and expanded and vacuum is carried out.

As the patient continues to walk, the weight will have to be exerted towards the front part of the vacuum unit (1) foot. During this position, if there is a volume that is ready to be compressed inside the front angular volume (OAH) the upper body shall move towards this volume. By this motion the downwards motion of the piston head (5) will be continued and the vacuum value of the air trapped inside will be increased. The patient then can lean at an angle on his/her prosthesis foot having a vacuum unit (1) as if said prosthesis is his/her natural foot.

Following the completion of the step taken, the force exerted at the tip of the toes of the prosthesis foot, which is left behind, is also cut off. By this means the lower body (3) is balanced by the tightening means (16) and the reopening of the front angular volume (OAH) is thus enabled. The lower body (3) that moves such that it opens the front angular volume (OAH) enables the piston head (5) to move upwards again and discharges the air.

By supporting the movement inside the step taking process explained above together with air pressure, absorbing the load of the patient's weight with some air movements can be provided. However this effect needs to be adjusted so that it is suitable to the body weights of the patients which can vary. Thus a front screw (14) is used which adjusts the pre tightening amount of the tightening means (16), located across the front angular volume (OAH) of the lower body (3). When the front screw (14) is tightened the tightening means (16) located on top shall also be tightened and this shall cause the limited movements of the bodies (2 and 3) inside the front angular volume (OAH) in relation to each other.

A similar action shall be used in order to limit the rear angular volume (AAH) motions located again in the heal section. Another tightening means (16) located inside the rear angular volume (AAH) shall be subjected by the rear screw (15) to be pre tightened thus enabling adjusting of the screw. By this means the force exerted by the patient onto the heel and the tightening amount of the rear angular volume (AAH) shall be adjusted.

The vacuum unit (1) subject to the invention is basically a vacuum pump driven by the angular motion of the ankle, located between the stump and the prosthetic feet. For this reason when it is used together with composite feet which do not have ankle shafts (4) the angularly driven lower body (3) of the vacuum unit (1) shall be a foot component which is parallel to the ground. According to the above mentioned embodiment of the invention, the lower body (3) is the component right below the upper body (2) and it is actually the sole of the feet stepping on the ground.

Figure 1:
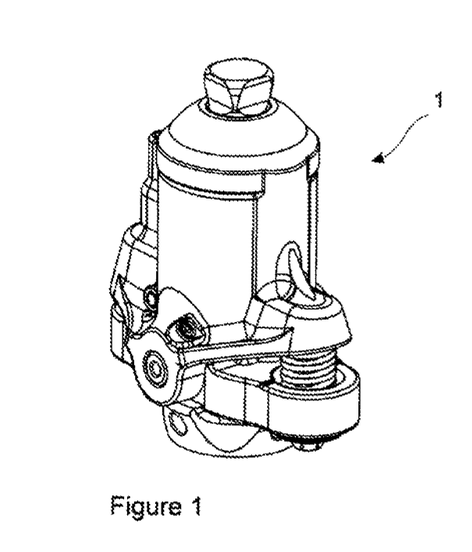
FIG. 1—Is the top back perspective view of the vacuum unit subject to the invention.
Figure 2:
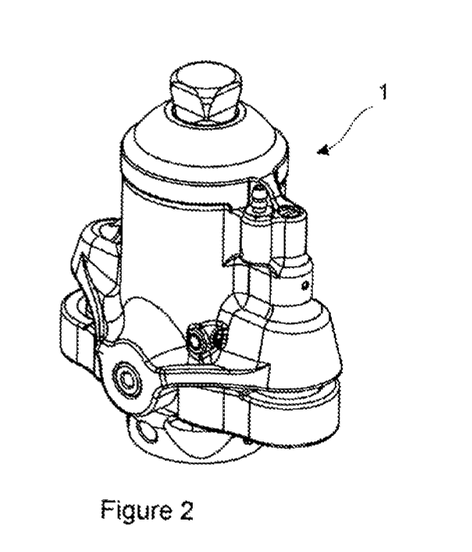
FIG. 2—Is the top front perspective view of the vacuum unit subject to the invention.
Figure 3:
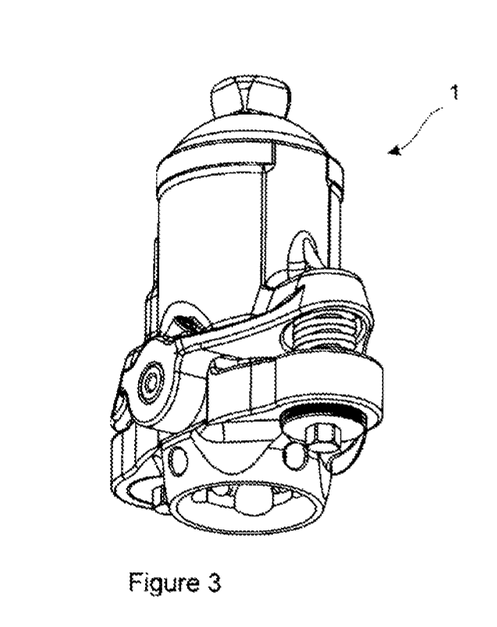
FIG. 3—Is the bottom back perspective view of the vacuum unit subject to the invention.
Figure 4:
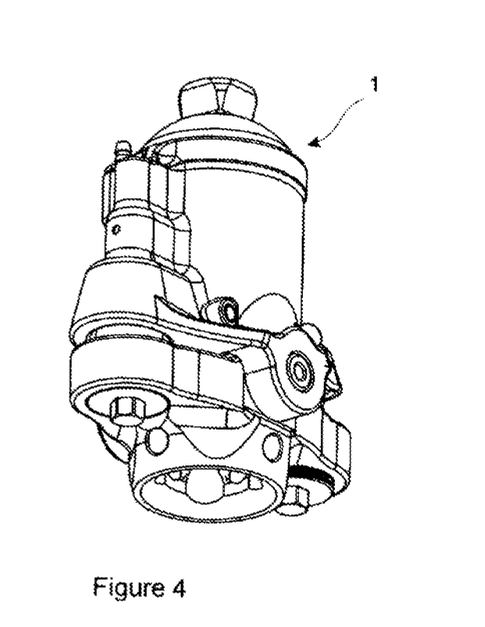
FIG. 4—Is the bottom front perspective view of the vacuum unit subject to the invention.
Figure 5:
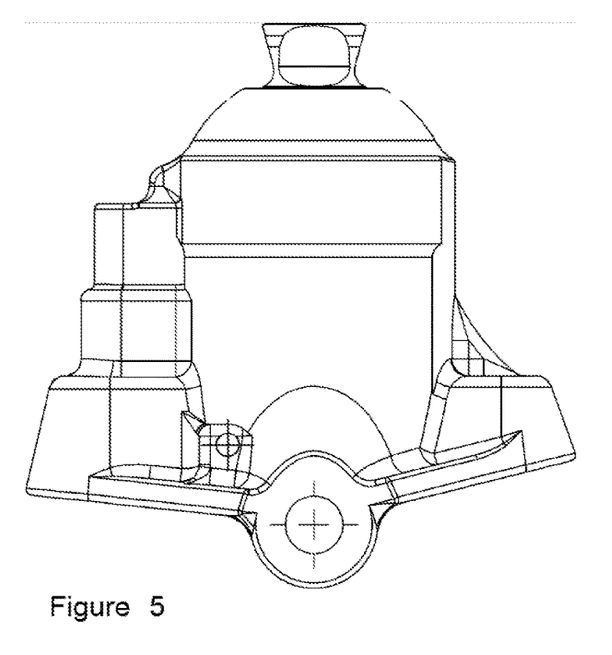
FIG. 5—Is the side view of the upper body of the vacuum unit subject to the invention.
Figure 6:
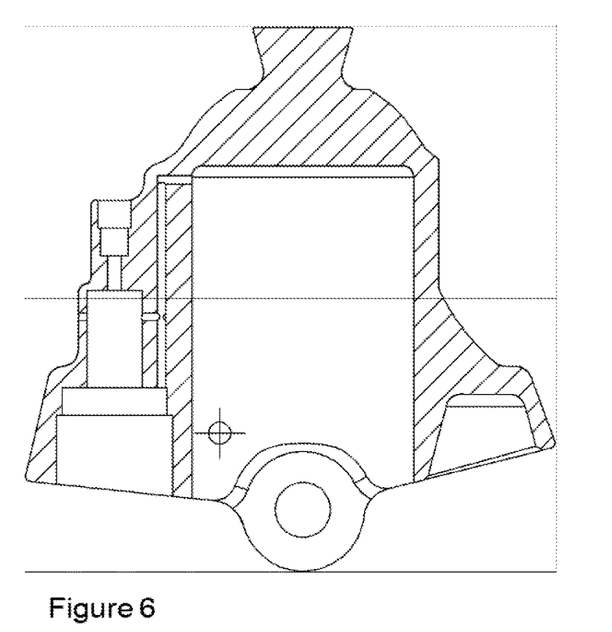
FIG. 6—Is the section view of the upper body without the side motion transfer group of the vacuum unit subject to the invention.
Figure 7:
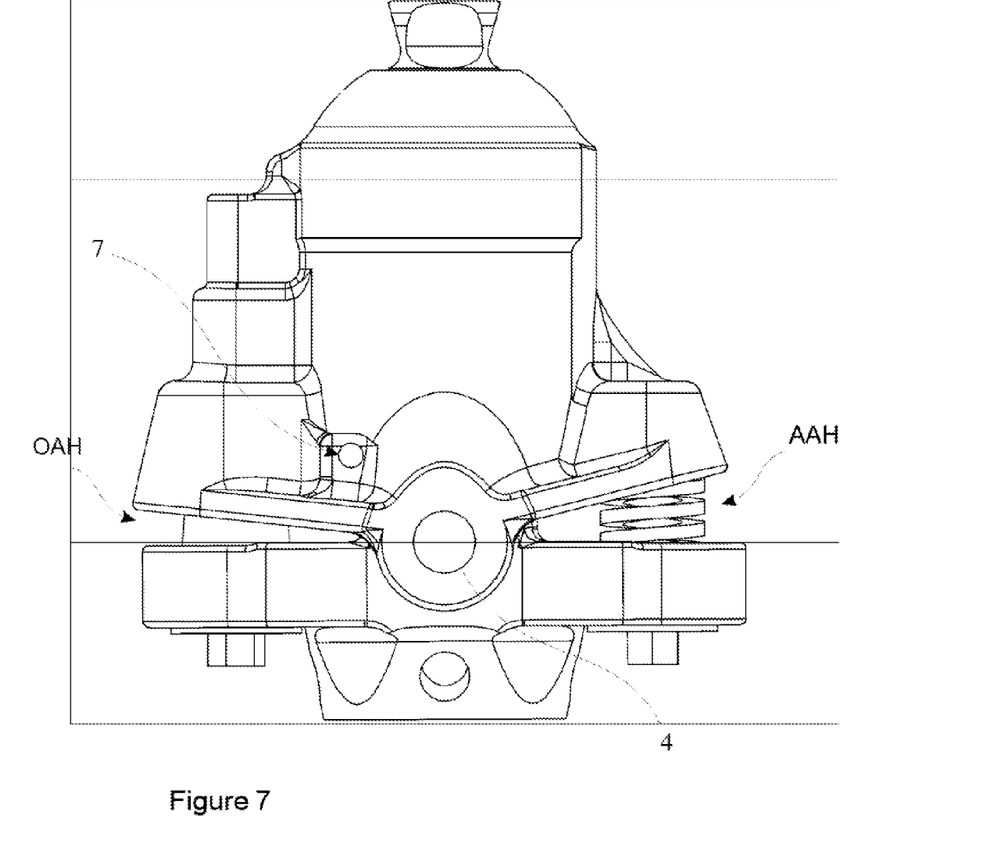
FIG. 7—Is the side view of the top and bottom body together of the vacuum unit subject to the invention.
Figure 8:
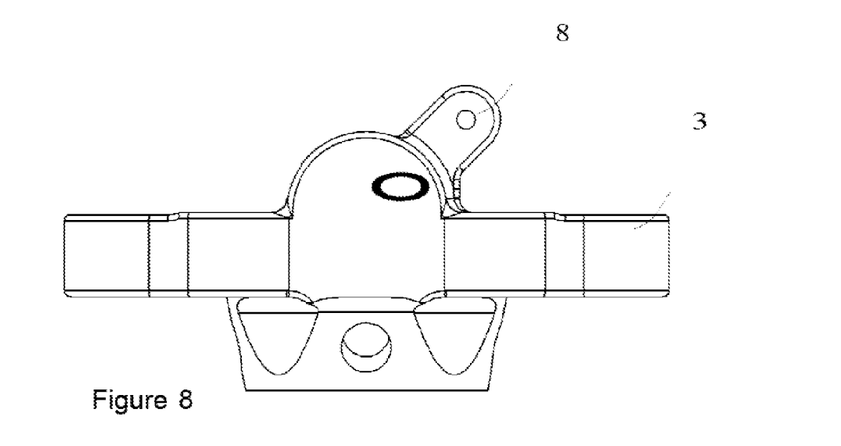
FIG. 8—Is the side view of the bottom body of the vacuum unit subject to the invention.
Figure 9:
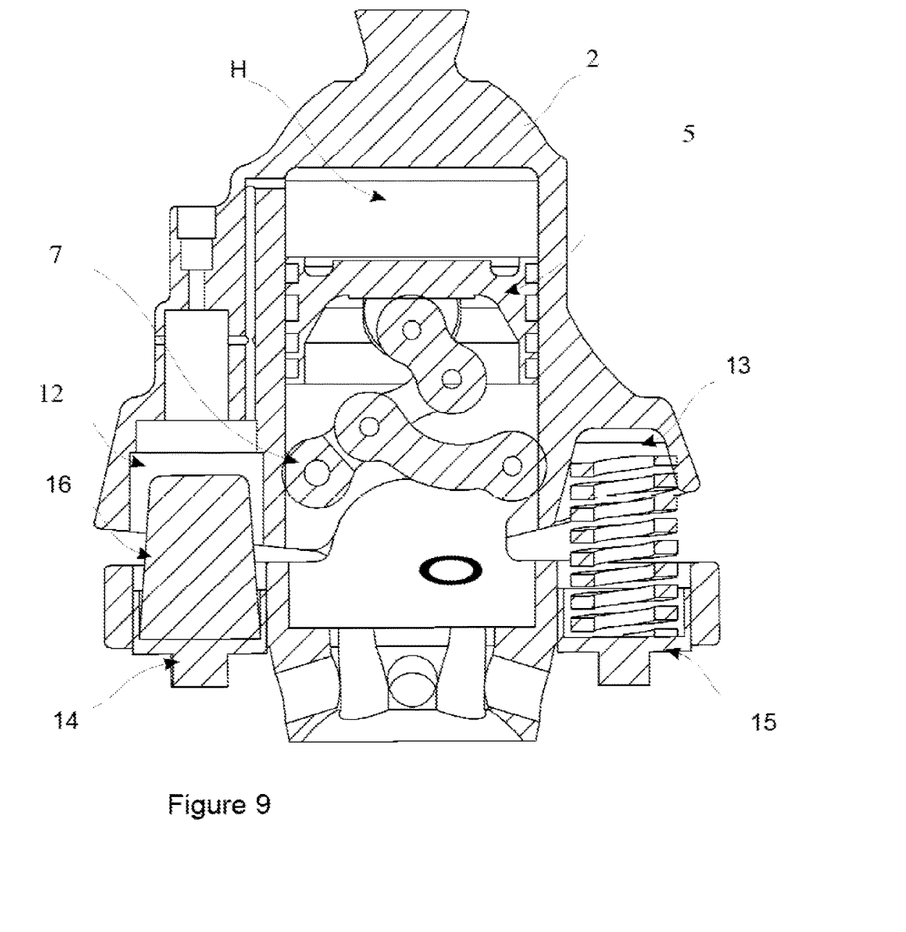
FIG. 9—Is the section view of both the upper and the bottom body of the vacuum unit subject to the invention.
Figure 10:
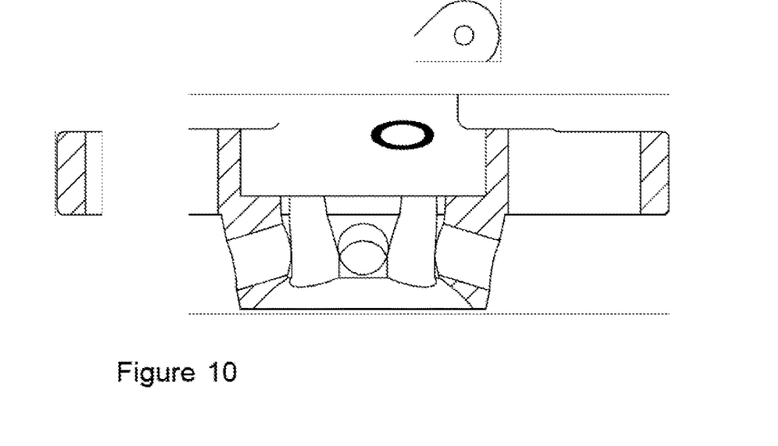
FIG. 10—Is the section view of the bottom body of the vacuum unit subject to the invention FIG. 11—Is the section view of the motion transfer group of the vacuum unit subject to the invention.
Figure 11:
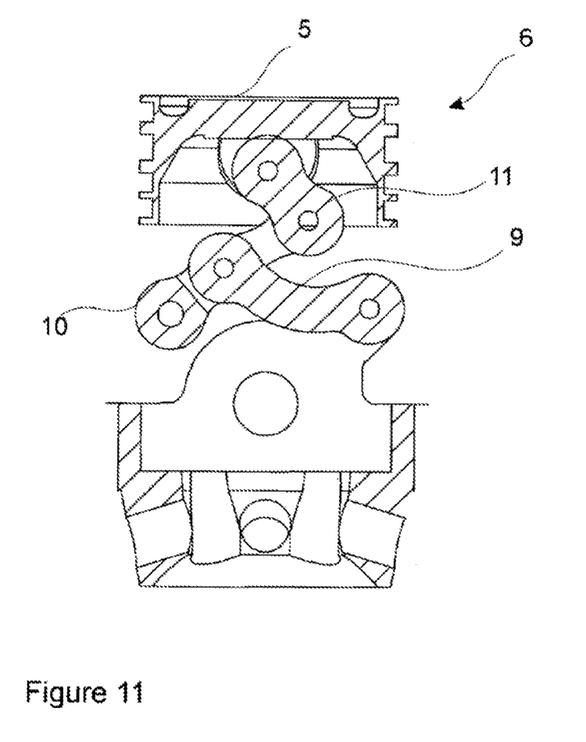
Figure 12:
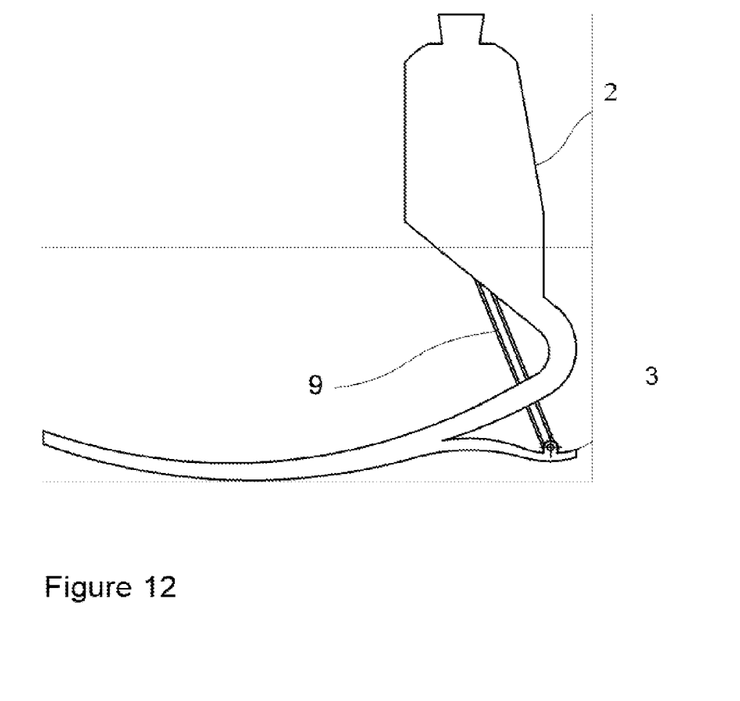
FIG. 12—Is the side view showing an application together with the composite foot of the vacuum unit subject to the invention.
Figure 13:
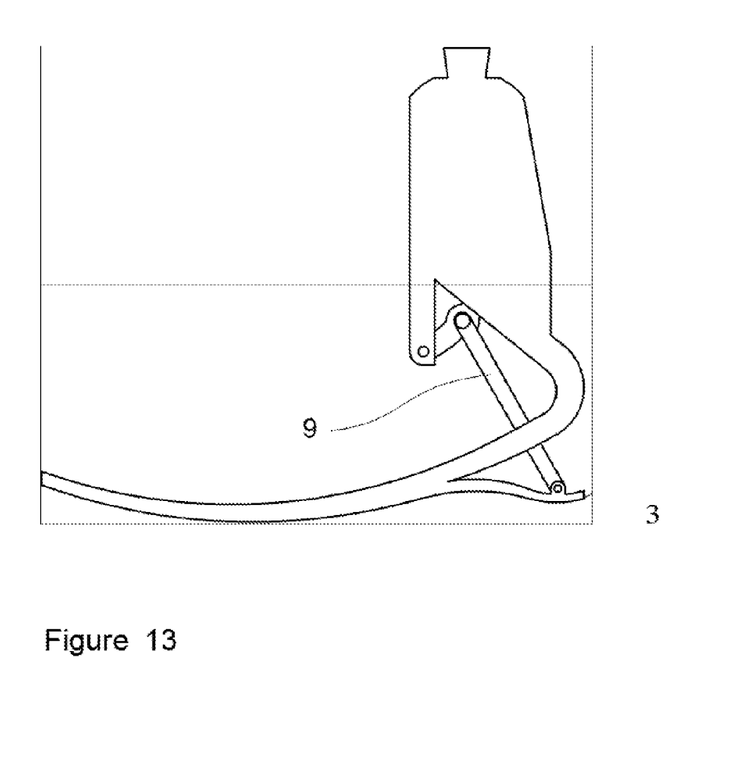
FIG. 13—Is the side view showing another application together with the composite foot of the vacuum unit subject to the invention.
Figure 14:
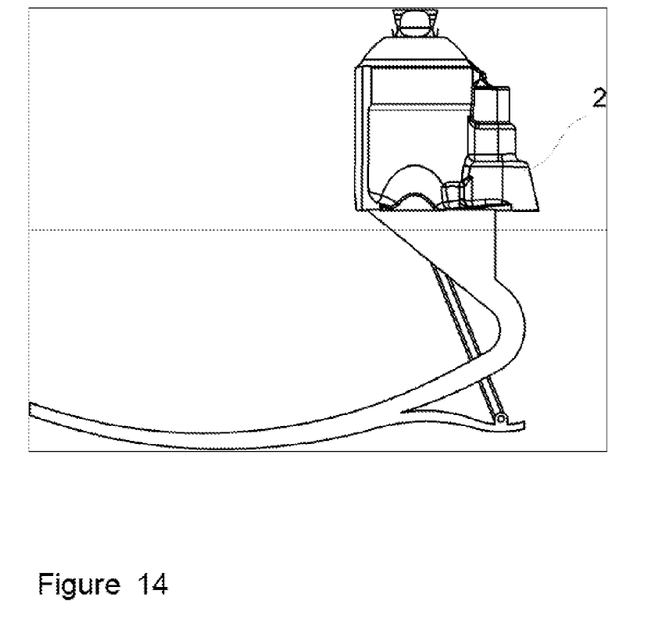
FIG. 14—Is the side view showing another application together with the composite foot of the vacuum unit subject to the invention.
Figure 15:
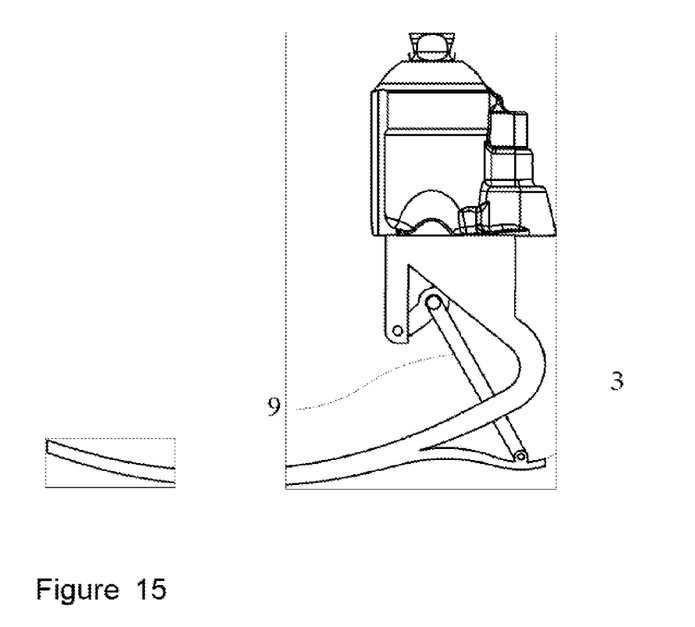
FIG. 15—Is the side view showing another application together with the composite foot of the vacuum unit subject to the invention.

In the case that the invention is used together with a composite type foot having an ankle, then the component parallel to the ground is the sole stepping on the ground. The driving of the forked chain link (10) shall be enabled by connecting the lower body chain link (9) to the sole and replacing the sole itself with the lower body (3). This application has been shown in the attached FIGS. 12-15.

What is claimed is:

1. A vacuum unit, for sucking out the air inside a prosthetic socket by means of ankle movements and which can be used as an ankle of a prosthetic leg, the vacuum unit comprising:
- an upper body with a front angular volume angled such that it shall allow an angular movement of a front side of a bottom face facing towards a lower body in order to increase a piston movement range, the upper body having a piston head inside it located on an ankle shaft, the upper body having a rear angular volume which allows the angular movement of a rear side of the bottom face, facing the lower body;
- wherein the lower body is capable of moving angularly in relation to the upper body and is located below the ankle shaft;
- a forked chain link pushed by a lower body chain link when a lower body connection gets closer to an upper body connection, wherein, the forked chain link moves upwards during a pushing motion, as one end of the forked chain link is connected to the upper body;
- a piston chain link that pushes the piston head in order to convert the upwards movement of the forked chain link into a linear motion that shall move the piston head upwards.

2. The vacuum unit according to claim 1, further comprising single direction valves arranged in order to provide a vacuum effect of an air pumping and suction motions created by the up and down movements of the piston head.

* * * * *